(12) United States Patent
Sheng et al.

(10) Patent No.: US 11,218,778 B2
(45) Date of Patent: Jan. 4, 2022

(54) METHOD TO AUTOMATICALLY HIGHLIGHT SPECIAL PROGRAM IN THE ELECTRONIC PROGRAM GUIDE (EPG) WHEN USER'S PHYSICAL CONDITION IS NOT HEALTHY

(71) Applicant: ARRIS Enterprises LLC, Suwanee, GA (US)

(72) Inventors: Libo Sheng, Shanghai (CN); Jianguo Zhou, Shanghai (CN); Fenggen Hu, Shanghai (CN)

(73) Assignee: ARRIS ENTERPRISES LLC, Suwanee, GA (US)

( * ) Notice: Subject to any disclaimer, the term of this patent is extended or adjusted under 35 U.S.C. 154(b) by 0 days.

(21) Appl. No.: 16/771,971

(22) PCT Filed: Dec. 18, 2017

(86) PCT No.: PCT/CN2017/116879
§ 371 (c)(1),
(2) Date: Jun. 11, 2020

(87) PCT Pub. No.: WO2019/119192
PCT Pub. Date: Jun. 27, 2019

(65) Prior Publication Data
US 2021/0219023 A1 Jul. 15, 2021

(51) Int. Cl.
*H04N 21/488* (2011.01)
*G16H 40/67* (2018.01)
(Continued)

(52) U.S. Cl.
CPC ....... *H04N 21/4882* (2013.01); *A61B 5/0022* (2013.01); *A61B 5/746* (2013.01);
(Continued)

(58) Field of Classification Search
None
See application file for complete search history.

(56) References Cited

U.S. PATENT DOCUMENTS 6,637,029 B1 * 10/2003 Maissel ............... H04N 21/454
725/46
6,973,621 B2 * 12/2005 Sie ......................... H04N 21/00
715/720

(Continued)

FOREIGN PATENT DOCUMENTS

| CN | 104469492 | 3/2015 |
| CN | 104888453 | 9/2015 |
| CN | 105187743 | 12/2015 |

OTHER PUBLICATIONS

International Search Report dated Sep. 17, 2018 in International (PCT) Application No. PCT/CN2017/116879.

*Primary Examiner* — Ricky Chin
(74) *Attorney, Agent, or Firm* — Wenderoth, Lind & Ponack, L.L.P.

(57) ABSTRACT

A system, method and computer readable media automatically highlights an unhealthy condition of a viewer. A set-top-box operatively connects to a network and a television display. The set-top-box is adapted to output a program to a viewer watching the television display. The set-top-box operatively connects through a wireless protocol to one or more wearable health monitoring devices that monitor one or more health readings associated with the viewer. The set-top-box outputs an alert to the viewer during the program if a health reading falls within a dangerous range. Advantageously, the alert is delivered through an EPG and may comprise pausing/stopping the program, and/or highlighting the alert on the television display for the viewer's safety.

20 Claims, 6 Drawing Sheets

(51) Int. Cl.
  *A61B 5/00* (2006.01)
  *H04N 21/41* (2011.01)
  *H04N 21/431* (2011.01)
  *H04N 21/4363* (2011.01)
  *H04N 21/45* (2011.01)
  *A61B 5/318* (2021.01)
  *A61B 5/0205* (2006.01)
  *A61B 5/021* (2006.01)
  *A61B 5/024* (2006.01)

(52) U.S. Cl.
  CPC ........... *A61B 5/7425* (2013.01); *G16H 40/67* (2018.01); *H04N 21/4126* (2013.01); *H04N 21/431* (2013.01); *H04N 21/43637* (2013.01); *H04N 21/4532* (2013.01); *A61B 5/021* (2013.01); *A61B 5/02055* (2013.01); *A61B 5/02438* (2013.01); *A61B 5/318* (2021.01); *A61B 5/681* (2013.01)

(56) References Cited

U.S. PATENT DOCUMENTS

| | | | | |
|---|---|---|---|---|
| 8,392,947 | B2* | 3/2013 | Grannan | H04N 21/4363 725/50 |
| 9,560,411 | B2* | 1/2017 | Seo | H04N 21/44218 |
| 9,579,060 | B1* | 2/2017 | Lisy | A42B 3/0453 |
| 2002/0059596 | A1* | 5/2002 | Sano | H04H 60/39 725/39 |
| 2003/0061618 | A1* | 3/2003 | Horiuchi | H04H 60/46 725/87 |
| 2003/0154482 | A1* | 8/2003 | Tsukamoto | H04N 21/47 725/53 |
| 2007/0240186 | A1* | 10/2007 | Silver | H04N 7/163 725/39 |
| 2009/0083799 | A1* | 3/2009 | Sakasegawa | H04N 5/4401 725/53 |
| 2009/0254944 | A1* | 10/2009 | Watson | H04N 21/4882 725/58 |
| 2012/0136217 | A1* | 5/2012 | Hyen | A61B 5/02055 600/300 |
| 2014/0229836 | A1* | 8/2014 | Young | H04N 21/47 715/721 |
| 2016/0066042 | A1* | 3/2016 | Dimov | H04N 21/44008 725/34 |
| 2016/0365006 | A1* | 12/2016 | Minturn | G09B 5/00 |
| 2016/0381415 | A1* | 12/2016 | Vijay | G06F 3/016 725/12 |
| 2017/0011210 | A1* | 1/2017 | Cheong | H04W 4/00 |
| 2017/0098465 | A1* | 4/2017 | Karve | H04N 21/44218 |
| 2017/0273629 | A1 | 9/2017 | Yu et al. | |
| 2018/0042542 | A1* | 2/2018 | Cronin | A61B 5/02405 |
| 2018/0048935 | A1* | 2/2018 | Ashoori | G16H 20/70 |
| 2018/0168464 | A1* | 6/2018 | Barnett, Jr. | A61B 5/6816 |
| 2020/0053312 | A1* | 2/2020 | Mukherjee | H04N 21/4854 |
| 2020/0214647 | A1* | 7/2020 | Peng | A61B 5/02 |
| 2021/0219023 | A1* | 7/2021 | Sheng | A61B 5/7425 |

* cited by examiner

METHOD TO AUTOMATICALLY HIGHLIGHT SPECIAL PROGRAM IN THE ELECTRONIC PROGRAM GUIDE (EPG) WHEN USER'S PHYSICAL CONDITION IS NOT HEALTHY

FIELD OF THE INVENTION

This disclosure relates to methods and systems for monitoring and alerting a program viewer of changes in physiological data through a set-top-box (STB); and more particularly, for monitoring vital statistics of a program viewer wearing a health monitoring device and automatically alerting the viewer of a change in physical condition through an Electronic Program Guide (EPG) output by the STB.

DESCRIPTION OF THE PRIOR ART

Horror, fantasy, suspense, supernatural fiction and thriller genres movies/programs generally seek to elicit a physiological reaction, such as an elevated heartbeat, through the use of fear and shock. However, often people do not realize that watching these types of movies/programs can put them at risk of aggravating preexisting health conditions, particularly cardiovascular problems. Currently no solution exists to intelligently highlight or warn susceptible users of viewing risks that particularly involve movies/programs so that the viewer can immediately stop the program and/or seek help.

Various systems implement a computer to monitor health information of a user. These types of systems have limited capabilities because they cannot operate when the computer is off on standby, or the user is not in the vicinity. To overcome these disadvantageous, systems have been proposed that provide healthcare monitoring through wearable devices, wireless sensors, home monitoring systems, and even set-top-boxes. Though these systems measure a user's healthy condition, they generally do not manage an STB to adjust the EPG and alert a viewer of media content of dangerous health condition changes.

Despite the efforts of prior art workers, there remains a need in the art for a system that operates through an STB that monitors the health of a viewer of movie/program content and alerts the viewer, and/or caregivers, when the viewer's physiological measurements fall within an unhealthy parameter. Furthermore, there remains a need in the art for a system that empowers an STB to intelligently monitor and alert a viewer through an EPG when he/she is not in healthy physical condition while watching media content.

BRIEF DESCRIPTION OF THE DRAWING

The invention will be more fully understood and further advantages will become apparent when reference is had to the following detailed description of the preferred embodiments of the invention and the accompanying drawing, in which.

DETAILED DESCRIPTION OF THE INVENTION

It is desirable to improve upon methods and systems for monitoring the health of viewers watching media content displayed on a television that elicits a physiological reaction in order to alert the user to a potentially dangerous health condition. These types of media generally include horror, suspense, fantasy, science fiction, supernatural and thriller programs that typically cause an elevated heartbeat, fear and anxiety in viewers. Users may not realize they are not in a healthy physical condition, and thus the subject system and method is provided to monitor user's physical conditions automatically. In doing so, the subject system and method helps users to avoid potential risks, such as being scared when in a non-healthy physical condition, potentially leading to a heart attack, for non-limited example. Advantageously, implementation of the subject system and method is carried out without the need for hardware upgrade in the STB, and is naturally integrated to current smart home and smart wearable devices.

The subject system and method monitors and alerts a viewer watching these types of programs of current changes in his/her physiological data gathered from a wearable device and transmitted to the user's set-top-box (STB) so that an alert is highlighted through the EPG and the viewer is notified. The STB gathers health data from the wearable device and/or health parameters and/or thresholds and monitors vital statistics of a viewer that is watching the program. Periodically during the program, at set time parameters, the STB may recall data from the wearable device. Alternatively, STB may continuously receive the health data from the wearable device throughout the length of the program. If a change in physical condition is detected, the change is compared to the thresholds either set by the STB or by the wearable device, if applicable. If the physical data falls within the threshold, the STB automatically alerts the viewer through an Electronic Program Guide (EPG) output by the STB. Throughout this application the terms "user" and/or "viewer" are used, which generally herein refer to the end user, consumer or television viewer currently watching a program. As used herein the terms "program", "movie" and/or "media content" may be used interchangeably to generally refer to, without limitation, media being viewed by a user/viewer. "Wearable health monitoring device" or "health monitoring device" includes devices that a user wears or carries on their person that monitors or tracks one or more physiological or neurological conditions, or medically useful health information.

Today many wearable devices are provided to monitor physiological signals of a wearer and/or operable through one's cellular phone device. Particularly, many of these devices monitor cardiovascular related stats for the user/wearer. For non-limiting example, these devices include those sold under the trade name: Withings Pulse O2 which support heart beat and SPO2 (Pulse Oxygen Saturation) found at http://www.withings.com/cn/zh/products/pulse; and Empatica E4 which monitors multi physiological signals (https://www.empatica.com/e4wristband). More and more physiological signals being monitored by wearable devices and their use are expected to increase in the consumer and medical fields. Included with monitoring of changes are neurological functions and movements, such as in monitoring and indicating the onset of seizures and/or stroke. Vast majorities of these wearable devices support hardware and software for sending data to other devices such as, for example, via a Bluetooth, Wi-Fi and/or through cellular data capabilities.

Through communication with a smart wearable device that monitors a user's physical condition, such as heart rate and/or abnormal movement patterns, the subject system, method and computer readable media provide the ability for an STB to warn the user when and if his or her physical condition is falling within or nearing a dangerous range. Smart wearable devices, usually presented as watches, are presently capable of monitoring a wearer's or user's health statistics. For example providing ECG/EKG (Electro-cardiogram), Blood Pressure, vital signs, abnormal body movement, diabetic sugar levels, and the like.

The present invention provides methods, systems, and computer readable media implemented through an STB operable to communicate with a health monitoring device to intelligently process and output an alert displayed through an EPG to a viewer of a movie/program/media content. Preferably, the subject method, system and computer readable media monitors vital statistics of a program viewer wearing a health monitoring device and automatically alerts the viewer of a change in physical condition through the Electronic Program Guide (EPG) output by the STB. A program viewer is alerted to changes in physiological data through the EPG output by the set-top-box (STB) to warn the viewer that his/her health condition falls within an unhealthy parameter. At which point, the STB may be programmed to perform a plethora of functions, including highlighting the alert to the viewer on the display screen and pausing or stopping the streaming of the program, issuing an alert warning sound, and/or communicating with other devices in the home to notify others of the viewer's health risk condition. Advantageously, the subject methods, systems, and computer readable media are generally operable with existing STBs without the need to add any additional hardware cost to the system.

In a first aspect of the invention an apparatus for automatically highlighting an unhealthy condition is provided. The apparatus comprises a set-top-box operatively connected to a network and a television display. The set-top-box is adapted to output a program to a viewer watching the television display. The set-top-box operatively connects through a wireless protocol to one or more wearable health monitoring devices that monitor one or more health readings associated with the viewer. The set-top-box is operative to output an alert to the viewer during the program if a health reading falls within a dangerous range.

In another aspect of the invention, there is provided a method for automatically highlighting an unhealthy condition. The set-top-box is connected to a network and a television display. The set-top-box is adapted to output a program to a viewer watching the television display. The set-top-box is connected, through a wireless protocol, to one or more wearable health monitoring devices that monitors one or more health readings associated with the viewer. The viewer is alerted during the program if a health reading falls within a dangerous range.

In another aspect of the invention one or more non-transitory computer readable media having instructions operable to cause one or more processors to perform the operations is provided. The readable media comprises: a) connecting a set-top-box to a network and a television display, wherein the set-top-box is adapted to output a program to a viewer watching the television display; b) connecting the set-top-box through a wireless protocol to one or more wearable health monitoring devices that monitors one or more health readings associated with the viewer, and c) alerting the viewer during the program if a health reading falls within a dangerous range.

The STB is connected with the smart wearable device via a communication protocol, such as Bluetooth or through a home network [Wi-Fi]. Body physical sensors are typically embedded in smart wearable devices to measure a user's blood pressure, heart beats, abnormal movement patterns, temperature etc. If the smart wearable device detects that some value is out of a configured threshold, for example the heart beat is too fast, an alert or notice will be transmitted to the STB and highlighted through the electronic program guide (EPG) for attention.

An EPG is a television guide application used with digital set-top boxes (STBs) and newer television sets that lists scheduled and current programs that are or will be available on each channel with a short summary or commentary. It is noted that the subject invention is not limited to digital STB/TV, but can also be applied to Internet Protocol television (IPTV) STB, Over-the-top content (OTT) STB, and other broadcasting of audio, video, and other media transmission technologies, etc. Content is provided through the STB and wireless network Wi-Fi enabled set-tops (STAs) communicable with Multiple System Operators (MSO(s)) providing multiple cable or direct-broadcast satellite television programs. Content may be provided through IPTV STB, OTT STB, etc. by way of Internet protocol, such as content transmission through services associated with the trade names Netflix, Amazon, YouTube, etc. Typically, the EPG includes options to set parental controls, order pay-per-view programming, search for programs based on theme or category, and set up to record programs. Through operation of the subject system and method, the EPG further includes an option to activate health monitoring. Alternatively, health monitoring can be set-up to automatically operate through the STB when the smart health device is located or within range.

A smart wearable device worn by a user is connected with the STB via a communication protocol. The Smart wearable device measures the user's blood pressure, heart beats, temperature and the like to form a baseline health report with configured thresholds. If the smart wearable device detects that some value is out of one or more of the configured thresholds, for example the heart beat is too fast, the app will notice the STB. In turn, the STB will highlight the special program in the EPG.

Accordingly, the subject system and method provides a communication platform between one or more wearable devices wherein the wearable device transmits health data to the STB and the STB in turn highlights unhealthy changes to the viewer watching a program. In general, the wearable device transmits physiological signal values to the STB. A corresponding threshold is predefined by the STB based on the health values. If the STB receives physiological signal values of the viewer that are out of thresholds, the STB will take proactive action to alert the viewer of his/her dangerous health condition. Preferably, the STB, through the EPG, highlights the risky health condition to the viewer on the display screen, and, optionally, others who are within the home. Optionally, the STB may further be programmed to automatically stop/pause the playing content/program when the viewer's physiological signal values are out of thresholds, and turn on the lights if STB is connected into a smart home system. Moreover, the STB can be programmed to set off an alarm to notice other family numbers, or call a predefined emergency number if the viewer is in a critical threshold.

The subject system and method are directed toward an STB content based alert to the viewer of the dangerous health condition. While numerous other devices simply monitor and report when the health indicators aren't like earlier measurements, they do not provide a direct link between content being viewed, the health parameters, and alerting the viewer by way of highlighting the alert in the EPG, as well as other alert mechanisms. The subject system and method may record measurement of the difference in health readings across a particular piece of content. For example, while watching a movie, the STB program may record the subscriber's heart rate at a set time point (i.e. at the beginning of the program). If the STB receives data that the heart rate is shooting up too dramatically, compared to the beginning of the program (not compared to a personal baseline), then the alert mode is activated and the viewer is notified of the dangerous health change. The warning/alert information can be transmitted to other DTVs or STBs in the home to alert others/a caregiver of the viewer's risky health condition.

Figure 1:
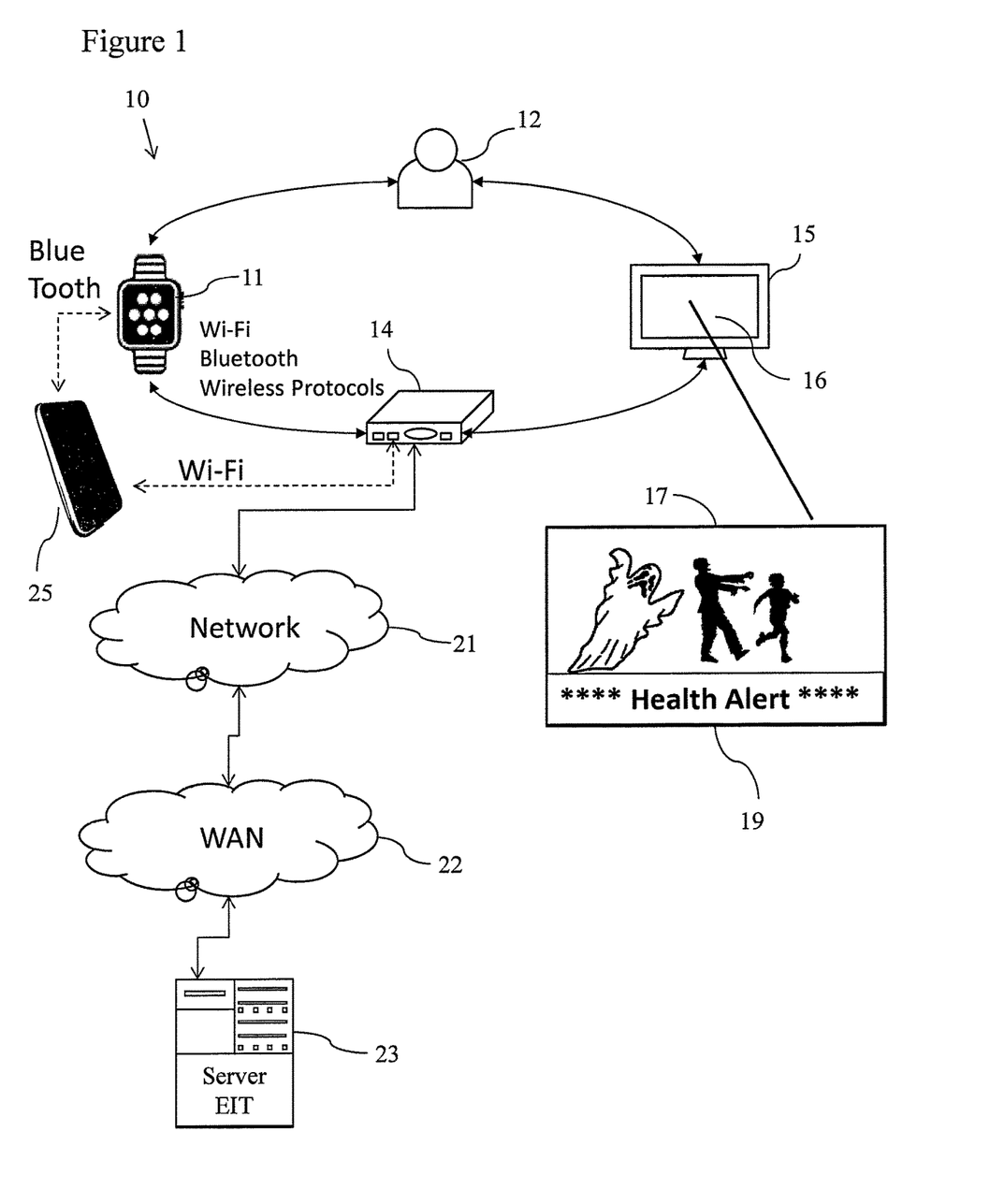
FIG. 1 is a schematic illustration of an embodiment of a system for STB healthcare monitoring and automatically alerting a viewer of a change in physical condition through an Electronic Program Guide (EPG) output by the STB.

FIG. 1 is a schematic illustration of an embodiment of a system for STB healthcare monitoring and automatically alerting a viewer of a change in physical condition through an Electronic Program Guide (EPG) output by the STB, shown generally at 10. A wearable device, shown generally at 11, is worn by a user 12. The wearable device 11 may be a smart watch, smart bracelet, blood pressure monitor operable with an app, or other type of wearable device that a user places on him/her person to collect data related to health and is capable of transmitting the information to another device.

In embodiments, the STB 14 may receive data and/or video services at a subscriber premise, and may output received multimedia content to a display device (e.g., TV 15). Content may be delivered to the STB 14 over one or more channels through a provider network 21 (e.g., hybrid fiber-coaxial network, fiber network, cellular network, high speed data network, or the like). Content may be provided by a wide-area network (WAN) 22, and a head end device may format and package the content for delivery over the provider network 21. For example, linear content (e.g., real-time content) associated with a channel may be delivered to the STB 14 over a specific frequency and/or wavelength associated with the channel. Besides the contents delivered over a specific frequency and/or wavelength, other communication protocols for secure communications over networks widely used on the Internet are contemplated. Such as, but not limited to, Hypertext Transfer Protocol (HTTP), etc., whereby content is generally delivered through the Internet with a specific URL, and no frequency or wavelength is needed. The wearable device 11 connects wirelessly to a STB 14 connected to TV 15.

The STB 14 may consult a program map table (PMT) to identify specific content received as a multimedia stream, along with EIT including rating information downloaded from one or more servers 23. For example, a tuner at the STB 14 may be tuned to a specific channel based upon a channel selection made at the STB 14 by user 12. The tuner may identify and prepare for processing multimedia content associated with an identified channel. In embodiments, the STB 14 parses EIT (including rating information) of the content. Preferably the STB's middleware i) downloads EPG information from the head end from the EIT data, ii) parses rating information stored in association with each program in the EIT and generates a modified EPG in a predetermined format that includes an indication that if the viewer selects a specific program, the health monitoring application will be/can be activated (See FIG. 3 for example of EPG).

Connection of the wearable device 11 may be through Blue tooth, Wi-Fi and/or other wireless protocols (e.g. NFC) or through a cellular device/cellular tablet as a mediator as shown generally at 25. Wherein the wearable device 11 has Wi-Fi capabilities, the wearable device 11 may directly connect to the STB 14 or may connect through the home gateway (GW), which in turn is connected to STBs a-n in the home. Alternatively, wherein the wearable device 11 has Blue tooth capabilities but the STB 14 does not, the wearable device 11 may connect through a wireless protocol, such as for example through cellular phone 25, which in turn connects via Wi-Fi/a wireless protocol to the STB. It is noted that wherein the STB does not have wireless connection capabilities, wireless connection is mediated through the home GW which, in turn, receives and process data from the wearable device 11 and transmits the data to the STB.

As user 12 starts to watch TV 15, powering on STB 14, the user's wearable device 11 connects to the STB through a communication protocol either directly or through the user's cellular device as a mediator, as discussed above. The system and method can be integrated into the software of the STB so that it can communicate and operate with existing smart home and/or smart wearable devices. Thus, it only entails software upgrade of the STB, without the need to upgrade hardware components. While typically existing gateways and access points in communication with STB devices include Wi-Fi capability, many standard IPTV Home Devices (Gateways/Access points/IP STBs) do not include blue tooth. Therefore, if the smart wearable device operates through blue tooth (and does not have Wi-Fi compatibility) an upgrade hardware component may be added to the IPTV Home Devices (Gateways/Access points/IP STBs) of the STB, such as an adapter (Wi-Fi or blue tooth enabling adapter connected through USB or HDMI port).

Alternatively, since many smart wearable devices operate through a cell phone 25 (via hot spot (cellular data), Wi-Fi, and/or blue tooth) as a mediator, the IPTV Home Devices (Gateways/Access points/IP STBs) include app software downloadable onto the user's cell phone that is in communication with the IPTV Home Devices (Gateways/Access points/IP STBs) for communication of health indicators to the STB for alerting the user. An App is provided for download onto the cell phone/smart phone 25 or for download onto the smart wearable device itself which communicates with the Application software of the STB to monitor the user's health through the communication platform. The app software provides a common protocol for direct communication between the STB and the wearable device. Wherein communication between the STB and the wearable device mediates through the cell phone, automatic message-passing without user intervention is preferred.

When the user 12 selects a program and begins watching it on a screen 16 of TV 15 the communication between the user's wearable device 11 and the STB 14 may be automatic, regardless of the program rating and/or without initiation by the user 12. Alternatively, connection between the wearable device 11 and STB 14 may be initiated automatically when the program selected through the EPG falls within a PG rating or higher. Optionally, connection between the wearable device 11 and the STB 14 may be initiated by the user by way of a prompt that appears on the screen 16 of TV 15 when the user turns on the TV 15 and STB 14.

When the STB 14 is powered on it may immediately search for a nearby wearable device 11, and if in range, the STB 14 connects to the wearable device 11. Upon connection of the wearable device 11 and the STB 14, the wearable device 11 may transmit the health vital information of the user 12. This health vital information may include, for example, blood pressure and heart rate. The health information may include threshold parameters already, and in which case the thresholds/parameters are also transmitted to the STB 14. If the health information does not include thresholds/parameters the STB 14 program may parse the information to determine thresholds/parameters based on charts via height, weight, age, gender and resting heart rate (RHR) and elevated heart rate (HER); this can be determined based on input from the user as to age, weight, height and gender, which may be downloaded from the wearable device 11, or prompted for entry on the screen 16 of the TV 15. Heart rate charts can be programmed within the app in accordance, for example, with the National Institute of Health, the average resting heart rate. Once these parameters are entered and parsed based on typical non-moving heart rates for the user's specific age, weight, height and gender they are parsed against the user's 20 current heart rate or blood pressure. One or more thresholds are then set, which may be for example the current heart rate as compared to a dangerous heart rate for the user based on age, weight height and gender. If the user's 20 heart rate or blood pressure falls within the threshold, an alert is issued on the screen 16 of TV 15.

Preferably, communication is implemented in software embedded in the smart wearable device. In the software embedded in the smart wearable device, when some abnormal user's health status is detected, the software is programmed to send out the predefined message (e.g. too high blood pressure, or heart disease) to the connected STB. Data of detected health status is transferred from the wearable device to a predefined number. For example, 0x01 means high blood pressure; 0x02 means high heartbeat. The predefined number is sent out as a message containing the predefined number to the STB. The STB parses the received message and the health status number. It then takes corresponding actions configured through the user interface (UI), including providing a health status highlight message, or pausing the TV program, or other alert method.

As shown for representative example on screen 16, a horror TV program 17 is being viewed by user 12. Upon transmission of health results outside of the threshold or an increase of blood pressure within a given range, or wherein the STB received the predefined number indicating a dangerous health status, an alert 19 is shown on screen 16.

Figure 2:
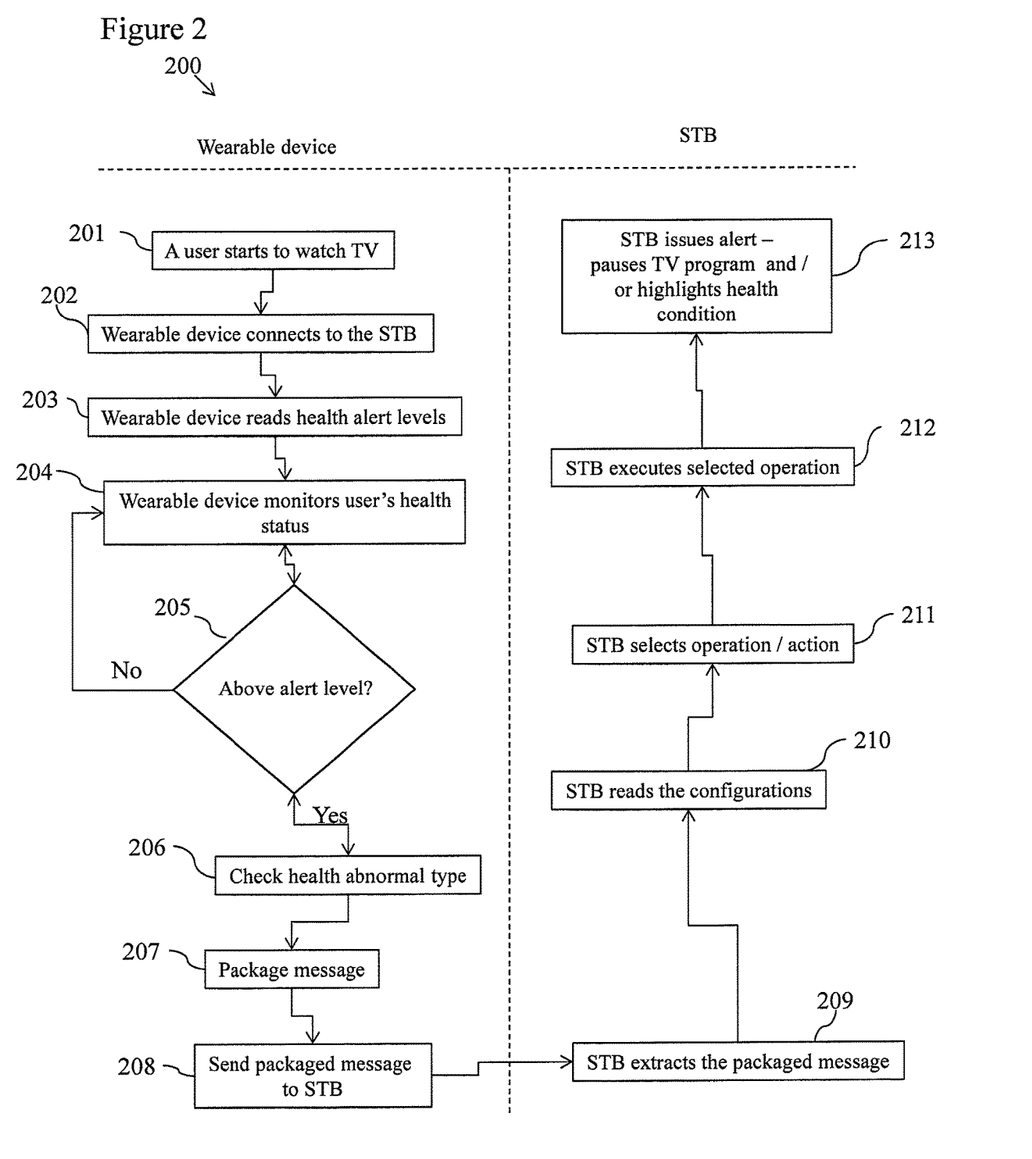
FIG. 2 is a flowchart illustrating steps of an embodiment of the subject method and system.

FIG. 2 is a flowchart illustrating steps of an embodiment of the subject method and system, shown generally at 200. As a user starts to watch TV, the user's wearable device connects to the STB through some communication protocols or through the user's cell phone if the wearable device can't connect to the STB directly, shown generally at 201 and 202, respectively. The wearable device, such as a smart watch is worn by a user watching a program on a TV display screen (computer, Smartphone, tablet and/or other display screens) with digital, IPTV, OTT, etc. content delivered by way of one or more STBs through a gateway operable by an MSO. Wearable device communicates with one or more STBs within range through a software application (app) and communication protocol, including Wi-Fi, Blue Tooth, cell phone mediation, and/or other wireless protocols (e.g. near field communication (NFC)). Upon pairing with the STB the wearable device transfers detected health status, or abnormal alert level values, defined by a predefined number entered through the application software of the STB communicated to the STB. For example, 0x01 means high blood pressure, 0x02 means high heart beat.

At 203 the wearable device then reads each health abnormal alert level value from the memory or from the connected STB and starts monitoring the user's health status. Settings in the UI may be provided so that the monitoring is automatic when the STB and/or TV is powered on, or alternatively, the monitoring may be automatic when content selected is set at a rating of PG or higher (for example), or the user may be prompted to start the monitoring.

At 204 the wearable device monitors the user's health status. At 205 the wearable device/or under instruction from the STB queries "is some health status above the alert level?" If "No", the wearable device continuously monitors the user's health status and continuously runs the query. If "Yes", at 206 the wearable device/the STB program checks the healths abnormal type (e.g. blood pressure, heartbeat, or other physiological data). At 207 a message containing the health abnormal type number is packaged, and at 208 sent to the connected STB.

At 209 the STB extracts the received message and also finds the health abnormal type number. The STB reads the configurations stored in the memory, at 210. The configuration defines the actions corresponding to different health abnormal type numbers.

At 211 the STB selects at least one operation/action (e.g. pausing TV and displaying alert message) related with the health abnormal type number extracted from the packaged message from the wearable device. The operation/action may be configured through the UI.

At 212 the STB executes the selected operation(s).

At 213 the STB issues an alert, for example pauses TV program and/or highlights health condition or alert message on the TV screen. Additionally, the STB may communicate with other STBs in the home to alert a caregiver in the home of the alert, and/or may interface with IP protocols to call one or more mobile devices of caregivers and (or an emergency number (i.e. 911). Health status may be presented as a highlighted message on the TV display screen, presented as a banner, or as an alert sound, pausing or stopping the TV program, alerting another device in the home system, in combination and/or other alert mechanism. An alert can be sent to one or more other devices in the home system. For example, an alert may be sent to other STB units to display the alert on TV screens in another room in a home to alert a family member or caregiver of the abnormal health condition.

In connection with the provision for monitoring of heart conditions, it is also contemplated that the subject systems and methods can provide for monitoring if someone is about to have a seizure. For example, some flashing programs or even video games can cause some people to have seizures. Some smart wearable devices (i.e. those sold under the Trademarks Smart Watch, Smart Monitor) monitor the onset of abnormal movement patterns similar to those caused by generalized tonic-clonic (GTC) seizures. The abnormal movement patterns can be assigned an abnormal alert level value to notify the STB, and thus the user and/or caregiver, that the user is dangerously close to having a seizure if the user continues with the stimuli-viewing the TV program, and/or playing the video game.

Figure 3:
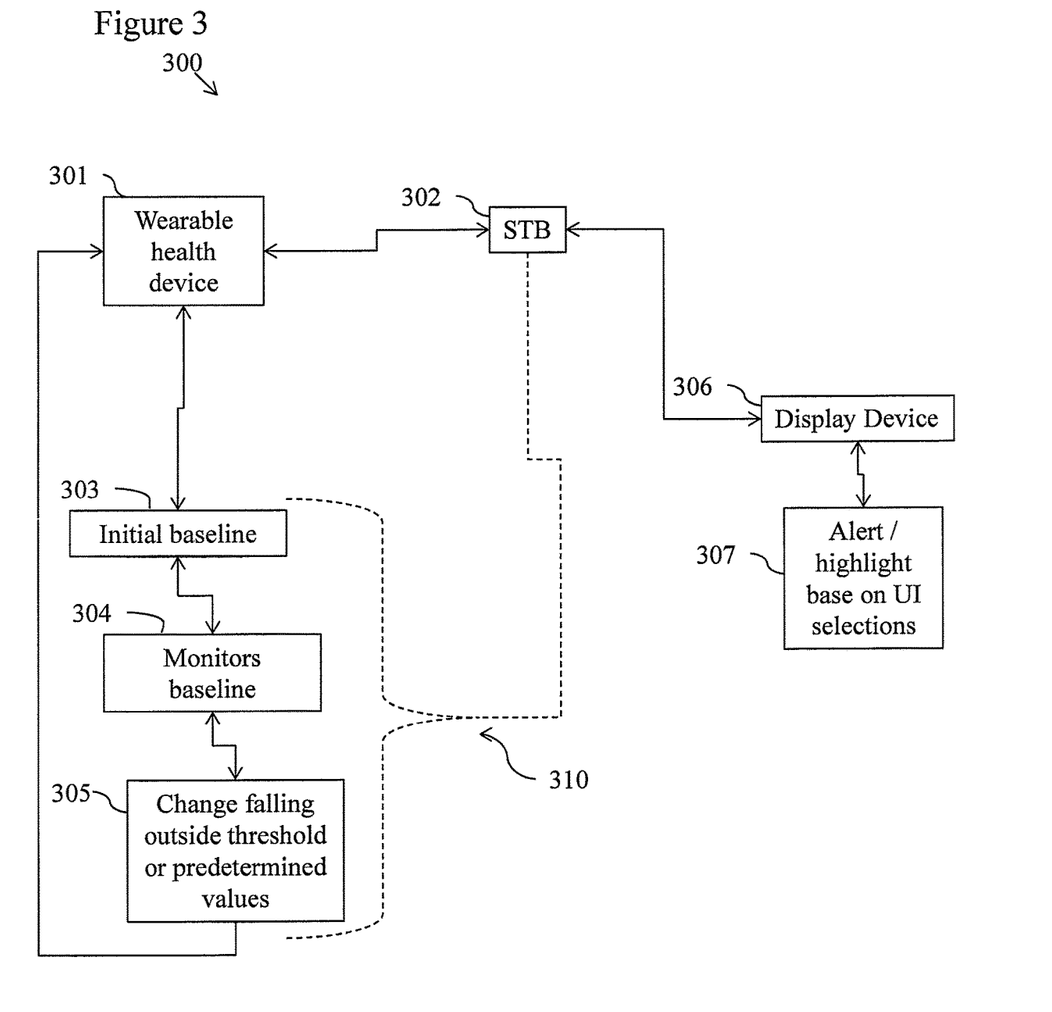
FIG. 3 is a flowchart illustrating steps of an embodiment of the subject method and system.

FIG. 3 is a flowchart illustrating steps of an embodiment of the subject method and system, shown generally at 300. A wearable health monitoring device 301 is connected with an STB 302 via a communication protocol [Wi-Fi; Blue Tooth; cell phone mediator]. The wearable device measures at least one physiological data stat of a user, such as for non-limiting example, blood pressure, heart beat, temperature or the like. The user's wearable device is uploaded with the user's health information and an initial set-up baseline health measurement for the user is recorded at 303. Monitoring of the user's health continues throughout the program, as shown at 304. If there is a change falling outside one or more physiological thresholds or predetermined values, as shown at 305, the wearable health device 301 sends the alert information to the STB 302. STB 302 outputs the alert on the display device 306 as an alert [pause; stop; alarm; banner]/highlight based on UI selections, at 307.

If the wearable device 301 does not have capability to set the initial baseline, and/or set thresholds or predetermined values and parse same against one another to determine that an alert must be issued, these functions can be programmed within the STB platform, as indicated generally at 310. In so doing, the STB program can include health guidelines. For example, UI entry for user X is age 65; the initial baseline for user X heartbeat recorded from the health device 301 is 130 at time y at the beginning of a horror program; the initial baseline is transmitted to the STB and recorded. At time y+30 minutes during the horror program, the wearable device transmits a heartbeat of 180. The STB parses the heart beat of 180 as against standards for 65 year olds and based on medical guidelines of Max Heart Rates. Max Heart Rates, for example, for 65 years olds generally provide a max threshold of 155 beats per minute. Because the heartbeat of 180 falls beyond the threshold, the STB 302 issues the alert output onto the display device 306. The STB may be programmed to include a notice to the user that the user's heart beat is approaching threshold levels. For example, if the user's heart beat is recorded as 151 beats per minute, the STB may issue a notice that the user is approaching threshold levels and the user should take a break. Each user's information—age, gender, height, weight, etc. can be entered upon set-up via the UI on the STB, as well as entry of alert options.

Figure 4:
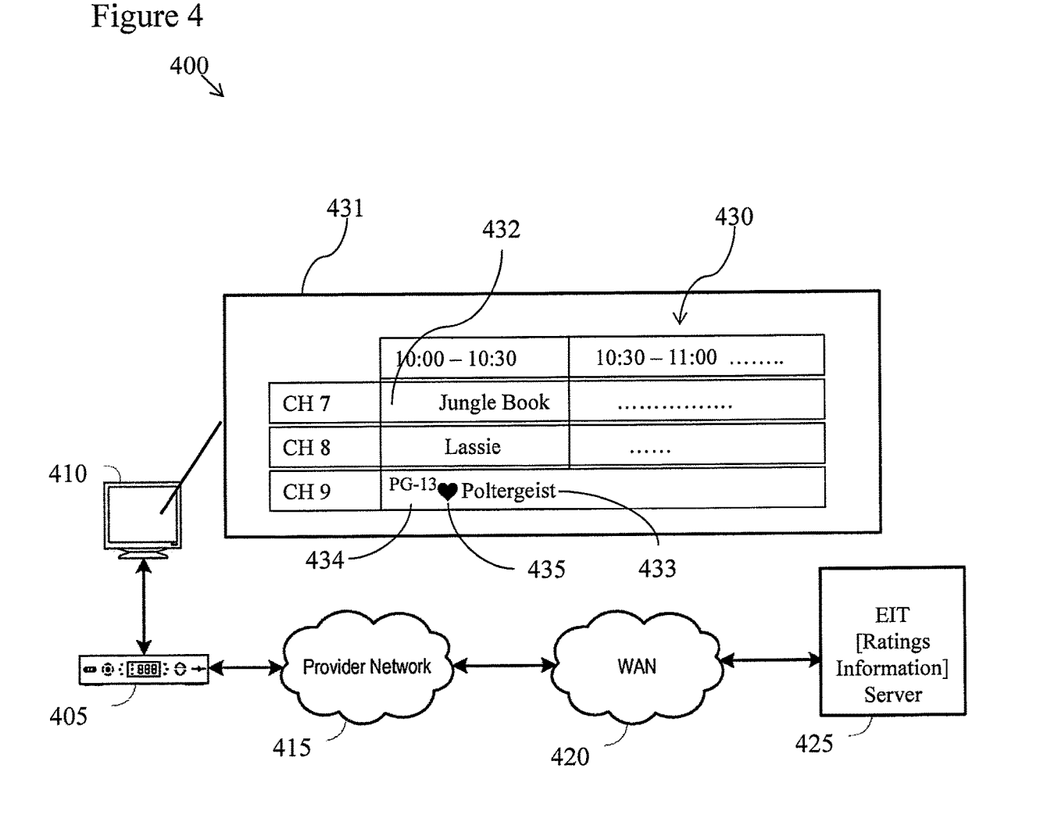
FIG. 4 is a schematic illustrating a representative EPG opened on a screen implementing an embodiment of the subject system and method integrating TV and/or movie film ratings.

FIG. 4 is a schematic illustrating a representative EPG opened on a screen implementing an embodiment of the subject system and method integrating TV and/or movie film ratings, shown generally at 400. A TV 410 displays a downloaded EPG displayed on a screen 431 to a user. A set-top box (STB) 405 receives data and/or video services and outputs the received multimedia content to the TV 410 and visa via display screen 431. Content may be delivered to the STB 405 over one or more channels through a provider network 415 (e.g., hybrid fiber-coaxial network, fiber network, cellular network, high speed data network, etc.). Content may be provided by a wide-area network (WAN) 420, and a head end device may format and package the content for delivery over the provider network 415. For example, linear content (e.g., real-time content) associated with a channel may be delivered to the STB 405 over a specific frequency and/or wavelength associated with the channel. Other communication protocols for secure communications over computer networks widely used on the Internet are also contemplated. Such as, but not limited to, Hypertext Transfer Protocol (HTTP), etc., whereby content is generally delivered through the Internet with a specific URL, and no frequency or wavelength is needed. The STB 405 may be a one-way STB configured to receive communications from the provider network 415 but without the ability to transmit upstream communications through the provider network 415.

In an alternative embodiment, programs are highlighted in the EPG screen if the wearable device detects an abnormal condition. In this manner, the ratings, etc. for each program may/or may not be utilized. Instead, the health condition based on the wearable device causes the alert or highlight on next to the listed programs on the EPG screen. When selecting a program through EPG (e.g. even not start playing), preferably programs (which may cause the viewers uncomfortable or dangerous) in EPG are highlighted if the wearable device detects abnormal condition.

Continuing with FIG. 4, in this embodiment, the STB consults a program map table (PMT) to identify specific content received as a multimedia stream, along with EIT including rating information downloaded from one or more servers 425. The STB's middleware i) downloads EPG information from the head end from the EIT data which includes rating information (such as Mature, Adults only, PG, PG-13, and the like), ii) parses rating information stored in association with each program in the EIT and generates a modified EPG in a predetermined format that includes an indication that if the viewer selects a specific program, the health monitoring application will be/can be activated.

Rating systems, for non-limiting example, include those set by the Motion Picture Association of America (MPAA) which provides a film rating system used in the United States and its territories to rate a film's suitability for certain audiences based on content. It is generally a voluntary rating system that is not enforced by law; films can be exhibited without a rating, although many theaters refuse to exhibit non-rated or NC-17 rated films. Other media, such as television programs and video games, are rated by the Entertainment Software Rating Board (ESRB), for example, and the TV Parental Guidelines. Typically, rating is assigned based on age and content (violence; nudity; etc.), for TV programs, computer and video games in the United States, Canada, and Mexico. Other rating systems are contemplated from other countries and territories and still would operate within the subject system and method.

Wherein a rating is provided, the subject system and method may automatically initiate the health monitoring application, or as set-up in the UI. For example, if a MPAA rating applies, the system may automatically be enabled when the rating is a PG or greater, or may be set by the UI. If an ESRB rating or the like applies, then the system may automatically be enabled when the rating is a rating pending (RP), mature (M), adult only (A), TV-MA—or other rating that indicates violence and/or nudity.

The STB 405 may store EIT including ratings information content for output to the display device TV 410. EIT content may include title, content descriptors, start times, end time and other types of multimedia including ratings information. Ratings information may be parsed from the EIT to be displayed in an EPG 430 next to the content listing as viewable in a blow-up of the display screen 431. Where the program content is not rated with violence/nudity, such as at 432, no rating may be shown. However, where program content, Poltergeist shown at 433, is rated with violence (nudity—such as rated PG-13—the rating is indicated at 434 with a health monitor indicator 435, which indicates to the user that health monitoring will be automatically activated (unless otherwise specified by way of the UI) if the program 433 is selected for viewing.

Figure 5:
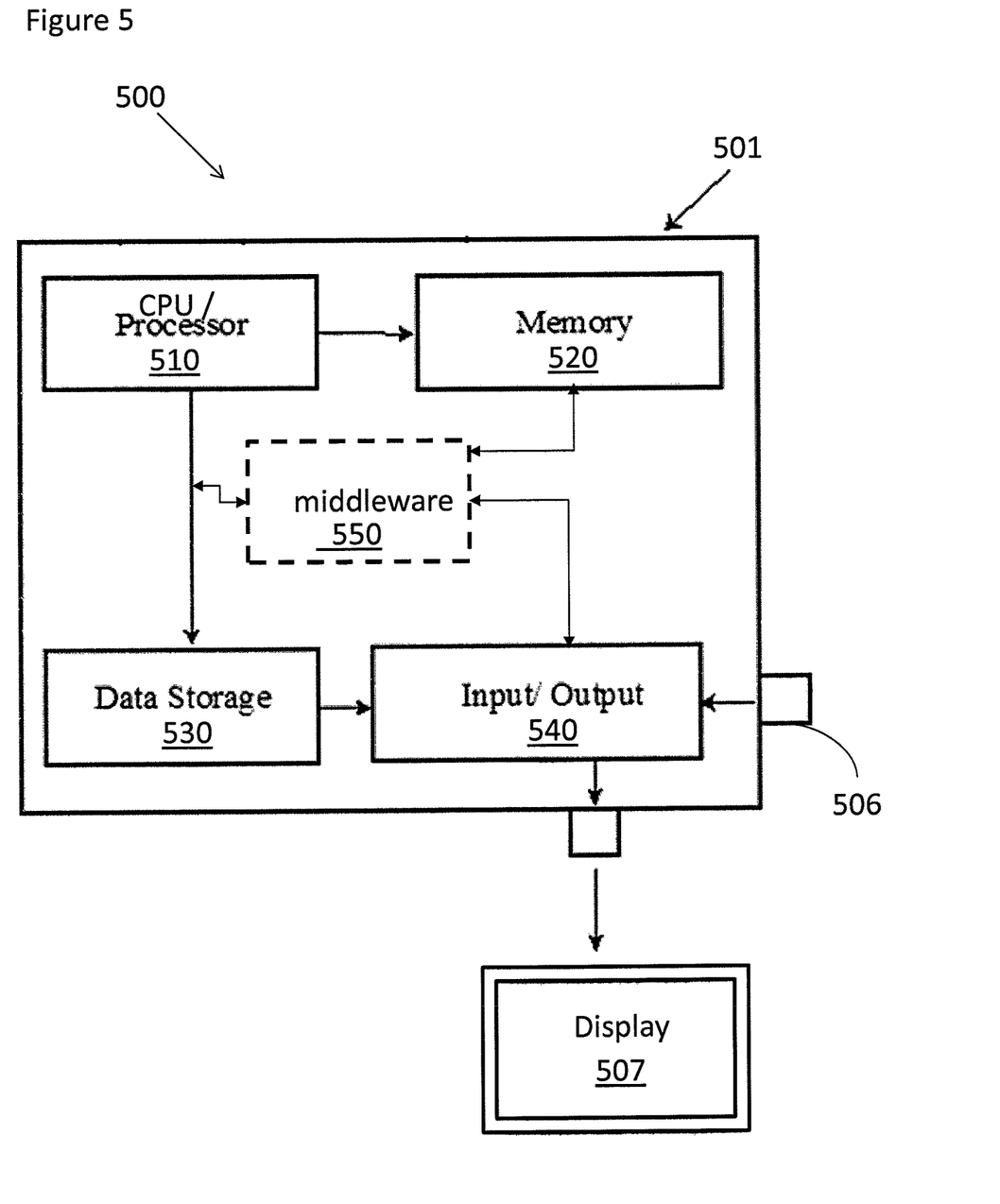
FIG. 5 is an architecture diagram of elements of a STB operable with the subject invention.

FIG. 5 is an architecture diagram of elements of a STB operable with the subject invention, shown generally at 500.

STB 501 is shown as a source device or apparatus for implementation of the subject invention. The STB 501 includes hardware generally configured with a module including a CPU/processor 510, a memory 520, a storage device 530, and an input/output device 540. Interface user application layer, middleware 550, is illustrated for functional purposes to aid in understanding the invention. Each of the components 510, 550, 520, 530, and 540 can, for example, be interconnected using a system bus. The processor 510 can be capable of processing instructions for execution of the subject method, system and computer readable media within the hardware configuration 500. STB 501 includes network connection to a service provider 506. STB 501 is connected through a high-definition multimedia interface (HDMI) 507 to a display device, herein a television. Besides HDMI, other ways to connect the STBs with display devices are contemplate, such as display ports, wireless connection, etc.

Figure 6:
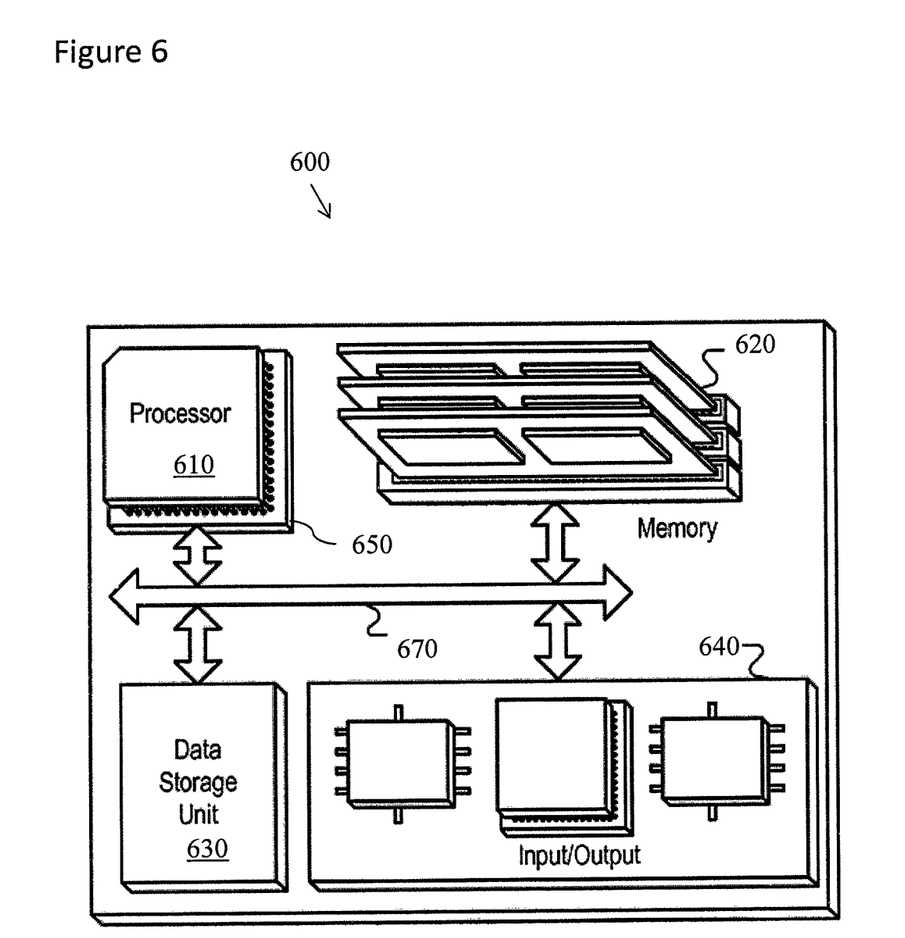
FIG. 6 is a block diagram of a hardware configuration operable to facilitate the initiation of the subject method.

FIG. 6 is a block diagram of a hardware configuration operable to facilitate the initiation of the subject method, shown generally at 600. The hardware configuration can include a processor 610, a memory 620, a storage device 630, decoder 650 and an input/output device 640. Each of the components 610, 620, 630, 650 and 640 can, for example, be interconnected using a system bus 670. The processor 610 can be capable of processing instructions for execution of the subject method, system and computer readable media within the hardware configuration 600. In one implementation, the processor 610 can be a single-threaded processor. In another implementation, the processor 610 can be a multi-threaded processor. The processor 610 can be capable of processing instructions stored in the memory 620 or on the storage device 630. The memory 620 can store information within the hardware configuration 600. In one implementation, the memory 620 can be a computer-readable medium. In one implementation, the memory 620 can be a volatile memory unit. In another implementation, the memory 620 can be a non-volatile memory unit. In some implementations, the storage device 630 can be capable of providing mass storage for the hardware configuration 600. In one implementation, the storage device 630 can be a computer-readable medium. In various different implementations, the storage device 630 can, for example, include a hard disk device, an optical disk device, flash memory or some other large capacity storage device. In other implementations, the storage device 630 can be a device external to the hardware configuration 600. The input/output device 640 provides input/output operations for the hardware configuration 600. In one implementation, the input/output device 640 can include one or more of a network interface device (e.g., an Ethernet card), a serial communication device (e.g., an RS-232 port), one or more universal serial bus (USB) interfaces (e.g., a USB 2.0 port), one or more wireless interface devices (e.g., an 802.11 card), and/or one or more interfaces for outputting video and/or data services to a CPE device (e.g., access point, cable modem, router, wireless extender, or other access device) or subscriber device (e.g, STB, etc.). In another implementation, the input/output device can include driver devices configured to send communications to, and receive communications from one or more networks (e.g., WAN, local network, cloud, headend/cloud controller, etc.).

The subject matter of this disclosure, and components thereof can be realized by software instructions that upon execution cause one or more processing devices to carry out the processes and functions described above. Such instructions can, for example, comprise interpreted instructions, such as script instructions, e.g., JavaScript or ECMAScript instructions, or executable code, SoftAp mode pulse timing activation and deactivation instructions, signal strength activation and deactivation software, initial fingerprint (birth certificate) algorithmic and execution instructions, activation signals or software, or other instructions stored in a computer readable medium.

Implementations of the subject matter and the functional operations described in this specification can be provided in digital/IP electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus.

A computer program (also known as a program, software, software application, script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification are performed by one or more programmable processors executing one or more computer programs to perform functions by operating on input data and generating output thereby tying the process to a particular machine (e.g., a machine programmed to perform the processes described herein). The processes and logic flows can also be performed by, and apparatus can also be implemented as, special purpose logic circuitry, e.g., an FPGA (field programmable gate array) or an ASIC (application specific integrated circuit).

Computer readable media suitable for storing computer program instructions and data include all forms of non-volatile memory, media and memory devices, including by way of example semiconductor memory devices (e.g., EPROM, EEPROM, and flash memory devices); magnetic disks (e.g., internal hard disks or removable disks); magneto optical disks; and CD ROM and DVD ROM disks. The processor and the memory can be supplemented by, or incorporated in, special purpose logic circuitry.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order unless otherwise noted, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter described in this specification have been described. Other embodiments are within the scope of the following claims. For example, the actions recited in the claims can be performed in a different order and still achieve desirable results, unless expressly noted otherwise. As one example, the processes depicted in the accompanying figures do not necessarily require the particular order shown, or sequential order, to achieve desirable results. In some implementations, multitasking and parallel processing may be advantageous.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An apparatus for automatically highlighting an unhealthy condition, comprising:
   a set-top-box operatively connected to a network and a television display, wherein the set-top-box is adapted to output a program to a viewer watching the television display;
   the set-top-box being operatively connected through a wireless protocol to one or more wearable health monitoring devices;
   the set-top-box being operative to monitor a health status of the viewer during the program;
   the set-top-box being operative to receive health data associated with the health status of the viewer during the program from the one or more wearable health monitoring devices;
   the set-top-box being operative to process the health data to determine when the health status of the viewer satisfies an abnormal condition;
   the set-top-box being operative to provide an alert in an electronic program guide (EPG) presented on the television display; and
   the set-top-box being operative to generate a health monitor indicator in a program listing in the EPG indicating that health monitoring is activated when a program having the health monitor indicator is selected for viewing.

2. The apparatus of claim 1, wherein the program is associated with a rating system wherein at least one rating indicates that the program includes content that may excite viewers, and the set-top-box's connectivity to the wearable health monitoring device is automatic.

3. The apparatus of claim 1, wherein the alert comprises stopping the program.

4. The apparatus of claim 3, wherein the set-top-box transmits the alert to one or more other devices.

5. The apparatus of claim 1, wherein the set-top-box is further operative to generate baseline health measurement using the received health data.

6. The apparatus of claim 1, wherein the set-top-box is further operative to highlight programs listing in the EPG that have a rating associated with potential risk of causing the abnormal condition.

7. The apparatus of claim 1, wherein the set-top-box is further operative to download EPG information associated with programs presented in the EPG, and parse the EPG information to generate the health monitor indicator in the program listing in the EPG.

8. A method for automatically highlighting an unhealthy condition comprising:
   connecting a set-top-box to a network and a television display, wherein the set-top-box is adapted to output a program to a viewer watching the television display;
   connecting the set-top-box through a wireless protocol to one or more wearable health monitoring devices;
   monitoring the viewer during the program;
   receiving, at the set-top box, health data associated with the health status of the viewer during the program from the one or more wearable health monitoring devices;
   processing, by the set-top box, the health data to determine when the health status of the viewer satisfies an abnormal condition;
   providing, by the set-top box, an alert in an electronic program guide (EPG) presented on the television display; and
   generating a health monitor indicator in a program listing in the EPG indicating that health monitoring is activated when a program having the health monitor indicator is selected for viewing.

9. The method of claim 8, wherein the program is associated with a rating system wherein at least one rating indicates that the program includes content that may excite viewers, and the set-top-box's connectivity to the wearable health monitoring device is automatic.

10. The method of claim 8, wherein the alert comprises stopping the program.

11. The method of claim 10, wherein the set-top-box transmits the alert to one or more other devices.

12. The method of claim 8 further comprising generating baseline health measurement using the received health data.

13. The method of claim 8 further comprising highlighting programs listing in the EPG that have a rating associated with potential risk of causing the abnormal condition.

14. The method of claim 8 further comprising downloading EPG information associated with programs presented in the EPG, and parsing the EPG information to generate the health monitor indicator in the program listing in the EPG.

15. One or more non-transitory computer readable media having instructions operable to cause one or more processors to perform the operations comprising:
   connecting a set-top-box to a network and a television display, wherein the set-top-box is adapted to output a program to a viewer watching the television display;
   connecting the set-top-box through a wireless protocol to one or more wearable health monitoring devices;
   monitoring the viewer during the program;
   receiving, at the set-top box, health data associated with the health status of the viewer during the program from the one or more wearable health monitoring devices;

processing, by the set-top box, the health data to determine when the health status of the viewer satisfies an abnormal condition;

providing, by the set-top box, an alert in an electronic program guide (EPG) presented on the television display;

generating a health monitor indicator in a program listing in the EPG indicating that health monitoring is activated when a program having the health monitor indicator is selected for viewing.

16. The non-transitory computer readable media of claim 15, wherein the program is associated with a rating system wherein at least one rating indicates that the program includes content that may excite viewers, and the set-top-box's connectivity to the wearable health monitoring device is automatic.

17. The non-transitory computer readable media of claim 15, wherein the alert comprises stopping the program.

18. The non-transitory computer readable media of claim 17, wherein the set-top-box transmits the alert to one or more other devices.

19. The non-transitory computer readable media of claim 15 further comprising generating baseline health measurement using the received health data.

20. The non-transitory computer readable media of claim 15 further comprising downloading EPG information associated with programs presented in the EPG, and parsing the EPG information to generate the health monitor indicator in the program listing in the EPG.

\* \* \* \* \*